United States Patent [19]
Jarvis et al.

[11] Patent Number: 5,928,932
[45] Date of Patent: Jul. 27, 1999

[54] ISOLATED GENE ENCODING AN ENZYME WITH UDP-GLUCOSE PYROPHOSPHORYLASE AND PHOSPHOGLUCOMUTASE ACTIVITIES FROM *CYCLOTELLA CRYPTICA*

[75] Inventors: Eric E. Jarvis, Boulder; Paul G. Roessler, Golden, both of Colo.

[73] Assignee: Midwest Research Institute, Kansas City, Mo.

[21] Appl. No.: 08/627,873

[22] Filed: Apr. 3, 1996

[51] Int. Cl.$^6$ .......................... C07H 21/04; C12N 15/00; C12N 1/20; C12N 9/12
[52] U.S. Cl. .................... 435/257.2; 536/23.6; 536/23.2; 435/6; 435/69.1; 435/71.1; 435/194; 435/252.3; 435/257.1; 435/320.1
[58] Field of Search .................................. 536/23.2, 23.6; 435/6, 69.1, 71.1, 194, 252.3, 257.1, 257.2, 320.1

[56] References Cited

FOREIGN PATENT DOCUMENTS

WO 87/05937  10/1987  WIPO .

OTHER PUBLICATIONS

Boles, E., Liebetrau, W., Hofmann, M. and Zimmermann, F.K. A family of hexosephosphate mutases in *Saccharomyces cerevisiae*. Eur. J. Biochem. 220:83–96 (1994).

Brautaset, T., Standal, R., Fjaervik, E. and Valla, S. Nucleotide sequence and expression analysis of the Acetobacter xylinum phosphoglucomutase gene. Microbiology 140:1183–1188 (1994).

Brown, L.M. Production of axenic cultures of algae by an osmotic method. Phycologia 21:408–410 (1982).

Dunahay, T.G., Jarvis, E.E. and Roessler, P.G. Genetic Transformation of Diatoms *Cyclotella cryptica* and *Navicula saprophila* J. Phycol. 31:1004–1012 (1995).

Elling, L. and Kula, M.R. Purification of UDP–glucose pyrophosphorylase from germinated barley (malt). J. Biotechnol. 34:157–163 (1994).

Fazi, A., Piaentini, M.P., Piatti, E. And Accorsi, A. Purification and Partial Characterization of the Phosphoglucomutase Isozymes from Human Placenta. Prep. Biochem. 20:219–240 (1990).

Galloway, C.M. and Dugger, W.M. Purification and characterization of phosphoglucomutase from peas. Physiol. Plant. 92:479–486 (1994).

Jarvis, E.E., Dunahay, T.G. and Brown, L.M. DNA Nucleoside Composition and Methylation in Several Species of Microalgae J. Phycol. 28:356–362 (1992).

Katsube, T., Kazuta, Y., Mori, H., Nakano, K., Tanizawa, K. and Fukui, T. UDP–Glucose Pyrophosphorylase from Potato Tuber: cDNA Cloning and Sequencing. J. Biochem. 108:321–326 (1990).

Kimura, S., Mitsui, T., Matsuoka, T. and Igaue, I. Purification, characterization and localization of rice UDP–glucose pyrophosphorylase. Plant Physiol. Biochem. 30:683–693.

Köplin, R., Arnold, W., Hötte, B., Simon, R., Wang, G. And Pühler, A. Genetics of Xanthan Production in *Xanthomonas compestris*: the xanA and xanB Genes are Involved in UDP–Glucose and GDP–Mannose Biosynthesis. J. Bacteriol. 174:191–199 (1992).

Kraft, R., Tardiff, J., Krauter, K.S. and Leinwand, L.A. Using Mini–Prep Plasmid DNA for Sequencing Double Stranded Templates with Sequenase. Biotechniques 6:544–546 (1988).

(List continued on next page.)

*Primary Examiner*—Robert A. Wax
*Assistant Examiner*—Tekchand Saidha
*Attorney, Agent, or Firm*—Edna M. O'Connor; Ken Richardson; Ruth Eure

[57] ABSTRACT

The present invention relates to a cloned gene which encodes an enzyme, the purified enzyme, and the applications and products resulting from the use of the gene and enzyme. The gene, isolated from *Cyclotella cryptica*, encodes a multifunctional enzyme that has both UDP-glucose pyrophosphorylase and phosphoglucomutase activities.

11 Claims, 4 Drawing Sheets

OTHER PUBLICATIONS

Lu, M. And Kleckner, N. Molecular Cloning and Characterization of the pgm Gene Encoding Phosphoglucomutase of *Escherichia coli*. J. Bacteriol. 176:5847–5851 (1994).

Marechal, L.R., Oliver, G., Veiga, L.A., Aida, A.P. and De Ruiz, H. Partial Purification and Some Properties of β–Phosphoglucomutase from *lactobacillus brevis*. Arch. Biochem. Biophys. 228:592–599 (1984).

Nakano, K., Omura, Y., Tagaya, M. and Fukui, T. UDP–Glucose Pyrophosphorylase from Potato Tuber: Purification and Characterization. J. Biochem. 106:528–532 (1989).

Peng, H.L. and Chang, H.Y. Cloning of a human liver UDP–glucose pyrophosphorylase cDNA by complementation of the bacterial galU mutation. FEBS Lett. 329:153–158 (1993).

Penger, A., Pelzer–Reith, B. and Schnarrenberger, C. cDNA Sequence for the Plastidic Phosphoglucomutase from *Spinacia oleracea* (L.). Plant Physiol. 105:1439–1440 (1994).

Purnelle, B., Skala, J., Van Dyck, L. and Goffeau, A. The Sequence of a 12 kb Fragment on the Left Arm of Yeast Chroosome XI Reveals Five New Open Reading Frames, Including a Zinc Finger Protein and a Homolog of the UDP–Glucose Pyrophosphorylase from Potato. Yeast 8:977–986 (1992).

Putt, W., Ives, J.H., Hollyoake, M., Hopkinson, D.A., Whitehouse, D.B. and Edwards, Y.H. Phosphoglucomutase 1: a gene with two promoters and a duplicated first exon. Biochem. J. 296:417–422 (1993).

Ragheb, J.A. and Dottin, R.P. Structure and sequence of a UDP–glucose pyrophosphorylase gene of *Dictyostelium discoideum*. Nucleic Acids Res. 15:3891–3906 (1987).

Rivera, A.A., Elton, T.S., Dey, N.B., Bounelis, P. And Marchase, R.B. Isolation and expression of a rat liver cDNA encoding phosphoglucomutase. Gene 133:261–266 (1993).

Roessler, P.G. Effects of Silicon Deficiency on Lipid Composition and Metabolism in the Diatom *Cyclotella cryptica*. J. Biol. Chem. 24:394–400 (1988).

Roessler, P.G. and Ohlrogge, J.B. Cloning and Characterization of the Gene that Encodes Acetyl–Coenzyme A Carboxylase in the Alga *Cyclotella cryptica*. J. Biol. Chem. 268:19254–19259 (1993).

Roessler, P.G. UDPGlucose Pyrophosphorylase Activity in the Diatom *Cyclotella cryptica*. Pathway of Chrysolaminarin Biosynthesis. J. Phycol. 23:494–498 (1987).

Sowokinos, J.R. Pyrophosphorylases in *Solanum tuberosum*. II. Catalytic Properties and Regulations of ADP–Glucose and UDP–Glucose Pyrophosphorylase Activities in Potatoes. Plant Physiol. 68:924–929 (1981).

Spychalla, J.P., Scheffler, B.E., Sowokinos, J.R. and Bevan, M.W. Cloning, Antisense RNA Inhibition and the Coordinated Expression of UDP–Glucose Pyrophosphorylase with Starch Biosynthetic Genes in Potato Tubers. J. Plant Physiol. 144:444–453 (1994).

Tamada, Y., Swanson, B.A., Arabshahi, A. and Frey, P.A. Preparation and Characterization of a Bifunctional Fusion Enzyme Composed of UDP–Galactose 4–Epimerase and Galatose–1–P Uridylyltransferase. Bioconjugate Chem. 5:660–665 (1994).

Uttaro, A.D. and Ugalde, R.A. A chromosomal cluster of genes encoding ADP–glucose synthetase, glycogen synthase and phosphoglucomutase in *Agrobacterium tumefaciens*. Gene 150;117–122 (1994).

Weissman, J.C. and Tillett, D.M. Design and Operation of an Outdoor Microalgae Test Facility. NREL/TP–232–4147:32–56 (1989).

Whitehouse, D.B., Putt, W., Lovegrove, J.U., Morrison, K., Hollyoake, M., Fox, M.F., Hopkinson, D.A. and Edwards, Y.H. Phospoglucomutase 1: Complete human and rabbit nRNA sequences and direct mapping of this highly polymorphic marker on human chromosome 1. Proc. Natl. Acad. Sci. U.S.A. 89:411–515 (1992).

Zhou, D., Stphens, D.S., Gibson, B.W., Engstrom, J.J., McAllister, C.F., Lee, F.K and Apicella, M.A. Lipooligosaccharide Biosynthesis in Pathogenic Neisseria. Cloning, Identification, and Characterization of Phosphoglucomutase Gene. J. Biol. Chem. 269:11162–11169 (1994).

Zrenner, R., Willmitzer, L. and Sonnewald, U. Analysis of the expression of potato uridinediphosphate–glucose pyrophosphorylase and its inhibition by antisense RNA. Planta 190:247–252 (1993).

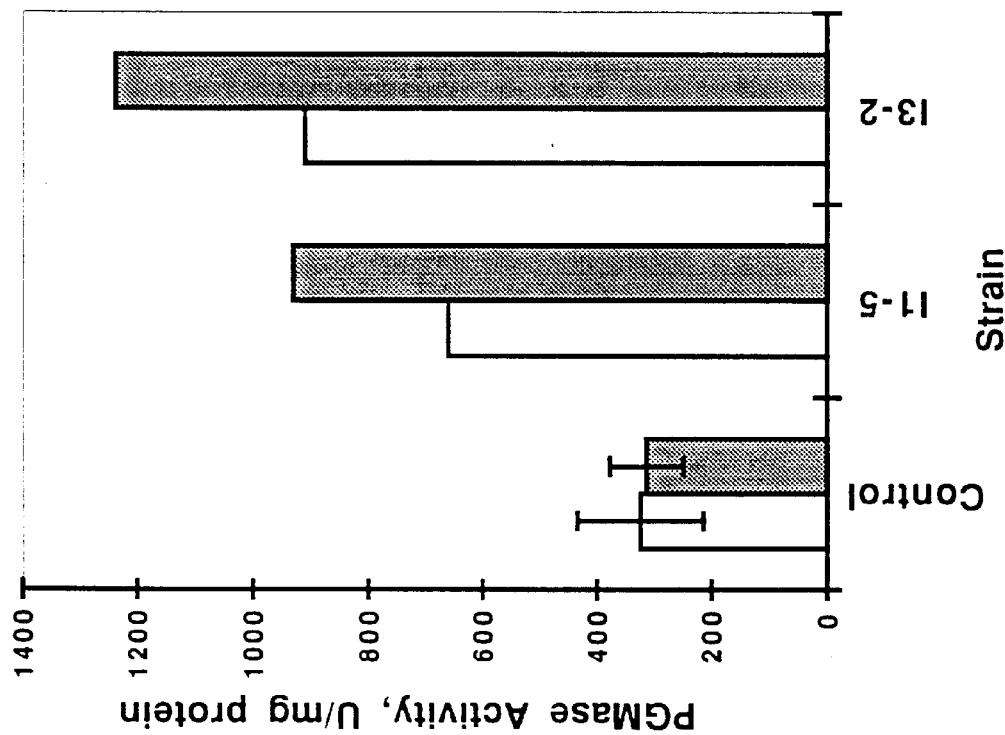
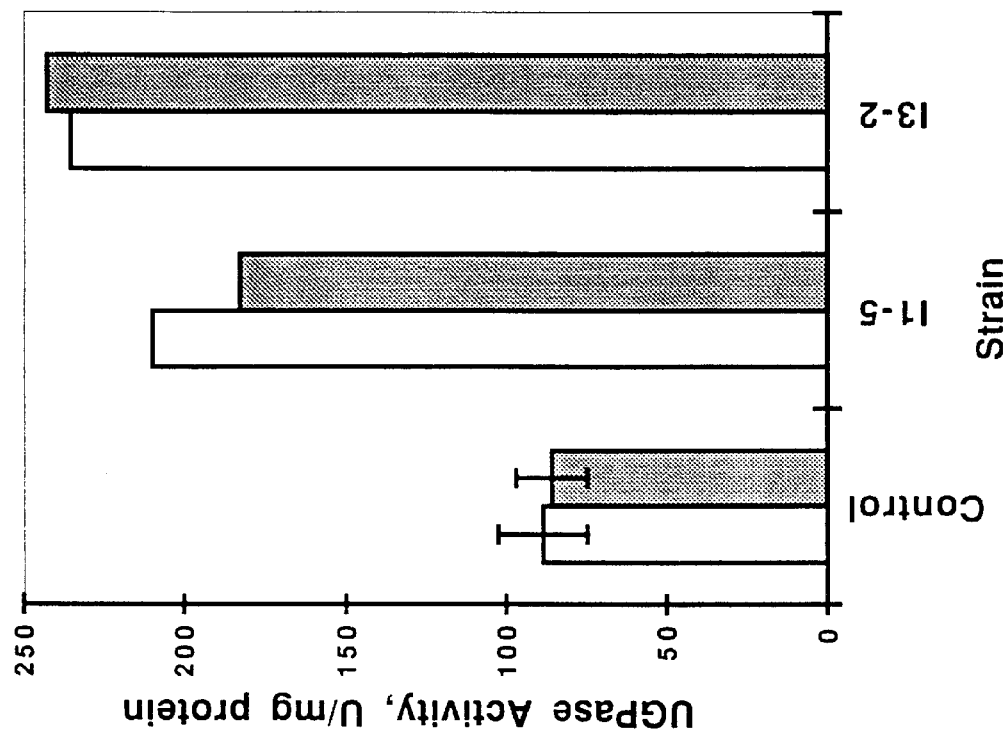

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (synthetic oligonucleotide)

(xi) SEQUENCE DESCRIPTION: SEQ ID NO:1:

ARRTTRTTNG TRTTRAA                                                              17

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (synthetic oligonucleotide)

(xi) SEQUENCE DESCRIPTION: SEQ ID NO:2:

TGGTAYCCNC CNGGWCA                                                              17

(2) INFORMATION FOR SEQ ID NO:3:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (synthetic oligonucleotide)

(xi) SEQUENCE DESCRIPTION: SEQ ID NO:3:

GCNGTYTCNA RYTG                                                                 14

(2) INFORMATION FOR SEQ ID NO:4:

(i) SEQUENCE CHARACTERISTICS:
        (A) LENGTH: 304 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

CGGAGACTTG TACGCTGCCC TCATCGGCTC AGGTCGTCTC TCTGCCCTCC TCGAAGGAGG        60

ATACAAGTAC ATGTTCGTCT CAAACTCTGA CAACCTTGGT GCCACCCTTG ACCTGAAAAT       120

CCTCACCCAC TTCGCCAAAA CGGATGCATC CTTTATGATG GAATGCTGTG AACGCACTGA       180

AAACGACAAG AAAGGAGGAC ATCTTGCTGT TCGTAATTCA GATCAACATT TGATCCTTCG       240

CGAATCTGCT ATGTGTGCCG ACGAAGACGA GCCTGCCTTC CAAGATATCA CCAAGCACCG       300

CTTC                                                                    304

(2) INFORMATION FOR SEQ ID NO:5:

(i) SEQUENCE CHARACTERISTICS:
        (A) LENGTH: 101 amino acids
        (B) TYPE: amino acid
        (D) TOPOLOGY: linear (ii) MOLECULE TYPE: protein (xi) SEQUENCE DESCRIPTION: SEQ ID NO:5:

Gly Asp Leu Tyr Ala Ala Leu Ile Gly Ser Gly Arg Leu Ser Ala Leu
 1               5                  10                  15

Leu Glu Gly Gly Tyr Lys Tyr Met Phe Val Ser Asn Ser Asp Asn Leu
                20                  25                  30

Gly Ala Thr Leu Asp Leu Lys Ile Leu Thr His Phe Ala Lys Thr Asp
            35                  40                  45

Ala Ser Phe Met Met Glu Cys Cys Glu Arg Thr Glu Asn Asp Lys Lys

```
                    50                  55                  60
Gly Gly His Leu Ala Val Arg Asn Ser Asp Gln His Leu Ile Leu Arg
 65                  70                  75                  80

Glu Ser Ala Met Cys Ala Asp Glu Asp Glu Pro Ala Phe Gln Asp Ile
                 85                  90                  95

Thr Lys His Arg Phe
            100
```

(2) INFORMATION FOR SEQ ID NO:6:

(i) SEQUENCE CHARACTERISTICS:
      (A) LENGTH: 3640 base pairs
      (B) TYPE: nucleic acid
      (C) STRANDEDNESS: double
      (D) TOPOLOGY: linear (ii) MOLECULE TYPE: DNA (genomic)

(ix) FEATURE:
      1.
          (A) NAME/KEY: CDS (exon)
          (B) LOCATION: 1..24
      2.
          (A) NAME/KEY: intron
          (B) LOCATION: 25..314
      3.
          (A) NAME/KEY: CDS (exon)
          (B) LOCATION: 315..782
      4.
          (A) NAME/KEY:intron
          (B) LOCATION: 783..885
      5.
          (A) NAME/KEY: CDS (exon)
          (B) LOCATION: 886..1402
      6.
          (A) NAME/KEY:intron
          (B) LOCATION: 1403..1478
      7.
          (A) NAME/KEY: CDS (exon)
          (B) LOCATION: 1479..3637

(xi) SEQUENCE DESCRIPTION: SEQ ID NO:6:

```
ATGGCGTCTT TTGAGCCCTG CAGGGTGAGA TTATGAATGA CACCGGAGTT TTCTCTCGTT     60
TGTCTGTTTT TTTAATCTGA TGGGGGAATG GGGAGTCTTA CGTTGGATTT CTTGGATGGG    120
GTGAATGCCT TGACGCTTGG ATACAATTGC AATGTTCGGG TCTTTATGTT CTATACTTTT    180
GTTCCTATCA CAGCTAATTT AACAAAACTC TCCCCTTTCA CTCCATATAT GCGACTGCTC    240
TACGCACGAC TACCAACGAT GGCACCGTAT TCTTATCGCT CCTCCCGATT AATGACGAAT    300
TGTCGTCACT TCAGACCAAG ATGGAGGCGG AGGGCATCGC CCAATCGGCC ATCTCCGCCT    360
TCGAATCCAC TTTTAACTCC CTCGTCTCCG GAAACACCGG CATCATCCCC GAATCAACCA    420
TCTCTCCTGT CCCGGAACTT GTGCACACCG ATTCCATCAC GGCTGAGCCC GATTCCTCCC    480
TGCTCGCTTC GACGGTGGTG CTGAAGCTCA ACGGTGGCCT GGGTACGGGC ATGGGGTTGG    540
ATAAGGCTAA GAGTCTTTTG GAGGTGAAGA ATGGAGATAC CTTTTTGGAT TTGACGGCTA    600
AGCAAGTCAT GTGCATGAGG GAGGAGTTTG ACAGAAGGT CAAGTTTATG TTGATGAACA    660
GTTTTTCGAC CTCGGATGAT ACTTTAGAGT TTTTTAGGAC CAAGTATCCT ACTCTTGCGG    720
CCGAAGAGGG GTTAGAGATG TTGCAGAATA AGGTGCCGAA GATTGATGCT ACAACTTATG    780
AGGTGGGTTG TTCGTTCCTC GTATGATTTA TTGTTTTTTA TTCGGGTTAT TGACAACGA     840
CTTGCCCGCG TTTTTTTCTA CTCTTACAAC TTAACCCGGT TACAGCCTGC CACCTGTCCC    900
TCCGACCCAA GCAACGAGTG GTGCCCTCCC GGTCACGGAG ACTTGTACGC TGCCCTCATC    960
GGCTCAGGTC GTCTCTCTGC CCTCCTCGAA GGAGGATACA AGTACATGTT CGTCTCAAAC   1020
```

```
TCTGACAACC TTGGTGCCAC CCTTGACCTG AAAATCCTCA CCCACTTCGC CAAAACGGAT    1080

GCATCCTTTA TGATGGAATG CTGTGAACGC ACTGAAAACG ACAAGAAAGG AGGACATCTT    1140

GCTGTTCGTA ATTCAGATCA ACATTTGATC CTTCGCGAAT CTGCTATGTG TGCCGACGAA    1200

GACGAGCCTG CCTTCCAAGA TATCACCAAG CACCGCTTCT TCAACACGAA CAATCTTTGG    1260

ATTCGCCTTG ACAAGTTGCA GGAGATTGTT GATAAATATG GAGGATTCAT TCCCCTCCCT    1320

ATGATCATGA ATGCCAAGAC CGTTGATCCC AAAGATGACA ACTCTCAAAA GGTTCTCCAA    1380

CTCGAAACTG CTATGGGTGC TGGTGAGTCC AACCTTGTAA AAACACTTCA GTCCATTTGT    1440

TAATACATCA CTCAGAGGTC TCTTATATTT CAAAACAGCC ATCGAATGCT TTGATGGTGC    1500

CAGCGCAGTG GTCGTGCCTC GTACTCGTTT CGCCCCCGTG AAGAAGTGCA ACGACCTTCT    1560

TCTTCTCCGC AGTGATGCTT ATGTCATCAC GGAAGATTTT CGTCCGGTGC TCAATCCTCT    1620

TTGCAATGGA GTTGCCCCCA TTATTGACCT GGATTCAAAG AAGTACAAGC TAGTCGGATC    1680

TCTGGAGGAA GCCACAGCCA ATGGGTGTCC TTCTCTTGTC GCTTGTAAGC GTCTGAAGGT    1740

CAAAGGCACC ATTCGCTTCG GCAGATCTAC CCGTTTTGTG GGAAATGTGT CTATCACTAA    1800

CTCGAGCGAT GAATCGAAGT ACGTCTCTGG AACAATGAG AATACAGATC TCGATGTGTC    1860

TGCTGATACT GGCCTGGGTC TTCTCAAGCC CACTCTTGTC AGAACTGCGC CTATTGCAGG    1920

CCAGAAACCT GGAACTTCCG GACTTCGCAA GAAGACTAAG GAGTTCATGT CGGAGAACTA    1980

TCTGAGCAAT TTTGTTCAGT CTGTATTCGA TGCTGTCATT GCTGCAGGAA CCAATGTCTC    2040

TGAAGGAACG CTCATGATTG GGGCGACGG GCGTTATTTC AACACTGAGG CTATTCAAAT    2100

TATCATTAAA ATGGGTGTTG CCAACGGGGT GAAGCGTTTC TGGATCGGAG AGAATGGGTT    2160

GCTCTCCACC CCTGCTGTCT CTGCCACAAT TCGAGAGCGT GGACCAGTAT GGCAAAAGTC    2220

CTTTGGTGCG TTCATCCTTA CCGCAAGTCA CAACCCTGGA GGCCCTGAGG AGGACTTTGG    2280

AATCAAGTAC AATACCCAGA ACGGAGGCCC TGCCCCCGAA TATCTCATGG AAGCAACTTA    2340

TGCCAACACT ACTTGCATCA AAACCTACAA GATTTGCGAG GACTTCCCCT CTATTGACAT    2400

AACTCAAGTC GGAGCTACCA CTGTTGCAGC CGCTGATGGA AGTACAAGTG TTGTTGTTGA    2460

GGTGATCCCC TCGACCCAGT CTCATGTTAC CCTACTGAAG ACCATCTTTG ACTTCCCTGC    2520

AATCAAGGCC CTTCTTGACC GTCCCGATTT TTCTATGGTC TACGACTCCA TGCATGGAGT    2580

TAACGGTCCT TTTTCCAAGG CTGTCTTCGT GGACGAACTT GGCCAGCCAG AGTCTGTACT    2640

CAGGAACCAT ATTCCTAAGG ACGACTTTGC CGGTGGACAT GCTGATCCCA ACCTTACTTA    2700

CGCCAAAGAG CTCGTGAAGA CCATGGGCTT GGATAGGACT GGGAACAAGA TTGATGTTGA    2760

TGGACCCATC CCTTCTTTCG GTGCTGCTGC TGATGGAGAT GGTGACCGCA ACATGATCCT    2820

TGGGACACAG TTCTTCGTCA CACCCTCTGA TTCTCTAGCT GTAATTGTTG CCAATGCCAA    2880

CTGCATCCCA TTTTTCAGCT CCCAAGGTGG TCTCAAGGCC GTTGCTAGGT CCATGCCCAC    2940

AAGTGGAGCT GTAGACCGAG TAGCAAAGGA CTTGAACCTT GACTTCTTTG AAACACCTAC    3000

TGGATGGAAG TTTTTCGGCA ACCTGATGGA TTCCAAGGCC ATCTTTAAGG GCAAAGACTA    3060

CACCCCGTTC ATCTGCGGTG AAGAGAGTTT TGGTACTGGC TCTGATCATG TGCGTGAGAA    3120

GGACGGCATA TGGGCTGTTT TGGCATGGTT GAACATCTTG GCCGCCCACA CCCTGATGC    3180

ATCGAAGCCT CTGGTGACTG TTGAAGACAT TGTAAGGAAA CACTGGTCCA AGTATGGTCG    3240

CAACTACTAC TGCCGTTGGG ACTTTGAGGG TATGGATGCA GCGGGAGCCA ATGCCATGAT    3300

GGAGAAGATG CGCGCTGATG CAGCATCGAA CACTGGCCGT ACTGTTGGAA GTTACACTAT    3360

TGCTACTGCC GATGACTTTA GGTACGTTGA CCCCGTGGAT GGGTCTGTCG CTGCAAAACA    3420
```

```
AGGAATTCGC TTCCTCATGT CGGATGGATC AAGAGTTATT TTCCGTTTGT CGGGCACAGC    3480

GGGTTCAGGT GCTACTGTTC GCATGTACAT TGAGCAATAT GAAACGGAGA AGCTTGATCT    3540

GCCTGTTGCC TCTGCTCTAG AAGAGCTTAC CTCAATTGCA CTGCAATTAT GTGACATCAA    3600

GACGTTTTGC GGCACCGAAA CTCCAACTGT CATCACCTGA                          3640
```

(2) INFORMATION FOR SEQ ID NO:7:

(i) SEQUENCE CHARACTERISTICS:
        (A) LENGTH: 1056 amino acids
        (B) TYPE: amino acid
        (D) TOPOLOGY: linear (ii) MOLECULE TYPE: protein (xi) SEQUENCE DESCRIPTION: SEQ ID NO:7:

```
Met Ala Ser Phe Glu Pro Cys Arg Thr Lys Met Glu Ala Glu Gly Ile
 1               5                  10                  15

Ala Gln Ser Ala Ile Ser Ala Phe Glu Ser Thr Phe Asn Ser Leu Val
                20                  25                  30

Ser Gly Asn Thr Gly Ile Ile Pro Glu Ser Thr Ile Ser Pro Val Pro
            35                  40                  45

Glu Leu Val His Thr Asp Ser Ile Thr Ala Glu Pro Asp Ser Ser Leu
        50                  55                  60

Leu Ala Ser Thr Val Val Leu Lys Leu Asn Gly Gly Leu Gly Thr Gly
65                  70                  75                  80

Met Gly Leu Asp Lys Ala Lys Ser Leu Leu Glu Val Lys Asn Gly Asp
                85                  90                  95

Thr Phe Leu Asp Leu Thr Ala Lys Gln Val Met Cys Met Arg Glu Glu
               100                 105                 110

Phe Gly Gln Lys Val Lys Phe Met Leu Met Asn Ser Phe Ser Thr Ser
            115                 120                 125

Asp Asp Thr Leu Glu Phe Phe Arg Thr Lys Tyr Pro Thr Leu Ala Ala
        130                 135                 140

Glu Glu Gly Leu Glu Met Leu Gln Asn Lys Val Pro Lys Ile Asp Ala
145                 150                 155                 160

Thr Thr Tyr Glu Pro Ala Thr Cys Pro Ser Asp Pro Ser Asn Glu Trp
                165                 170                 175

Cys Pro Pro Gly His Gly Asp Leu Tyr Ala Ala Leu Ile Gly Ser Gly
            180                 185                 190

Arg Leu Ser Ala Leu Leu Glu Gly Gly Tyr Lys Tyr Met Phe Val Ser
        195                 200                 205

Asn Ser Asp Asn Leu Gly Ala Thr Leu Asp Leu Lys Ile Leu Thr His
    210                 215                 220

Phe Ala Lys Thr Asp Ala Ser Phe Met Met Glu Cys Cys Glu Arg Thr
225                 230                 235                 240

Glu Asn Asp Lys Lys Gly Gly His Leu Ala Val Arg Asn Ser Asp Gln
                245                 250                 255

His Leu Ile Leu Arg Glu Ser Ala Met Cys Ala Asp Glu Asp Glu Pro
            260                 265                 270

Ala Phe Gln Asp Ile Thr Lys His Arg Phe Phe Asn Thr Asn Asn Leu
        275                 280                 285

Trp Ile Arg Leu Asp Lys Leu Gln Glu Ile Val Asp Lys Tyr Gly Gly
    290                 295                 300

Phe Ile Pro Leu Pro Met Ile Met Asn Ala Lys Thr Val Asp Pro Lys
305                 310                 315                 320
```

```
Asp Asp Asn Ser Gln Lys Val Leu Gln Leu Glu Thr Ala Met Gly Ala
            325                 330                 335

Ala Ile Glu Cys Phe Asp Gly Ala Ser Ala Val Val Pro Arg Thr
            340                 345                 350

Arg Phe Ala Pro Val Lys Lys Cys Asn Asp Leu Leu Leu Arg Ser
            355                 360                 365

Asp Ala Tyr Val Ile Thr Glu Asp Phe Arg Pro Val Leu Asn Pro Leu
            370                 375                 380

Cys Asn Gly Val Ala Pro Ile Ile Asp Leu Asp Ser Lys Lys Tyr Lys
385                 390                 395                 400

Leu Val Gly Ser Leu Glu Glu Ala Thr Ala Asn Gly Cys Pro Ser Leu
                405                 410                 415

Val Ala Cys Lys Arg Leu Lys Val Lys Gly Thr Ile Arg Phe Gly Arg
                420                 425                 430

Ser Thr Arg Phe Val Gly Asn Val Ser Ile Thr Asn Ser Ser Asp Glu
            435                 440                 445

Ser Lys Tyr Val Ser Gly Thr Ile Glu Asn Thr Asp Leu Asp Val Ser
    450                 455                 460

Ala Asp Thr Gly Leu Gly Leu Leu Lys Pro Thr Leu Val Arg Thr Ala
465                 470                 475                 480

Pro Ile Ala Gly Gln Lys Pro Gly Thr Ser Gly Leu Arg Lys Lys Thr
                485                 490                 495

Lys Glu Phe Met Ser Glu Asn Tyr Leu Ser Asn Phe Val Gln Ser Val
                500                 505                 510

Phe Asp Ala Val Ile Ala Ala Gly Thr Asn Val Ser Glu Gly Thr Leu
            515                 520                 525

Met Ile Gly Gly Asp Gly Arg Tyr Phe Asn Thr Glu Ala Ile Gln Ile
    530                 535                 540

Ile Ile Lys Met Gly Val Ala Asn Gly Val Lys Arg Phe Trp Ile Gly
545                 550                 555                 560

Glu Asn Gly Leu Leu Ser Thr Pro Ala Val Ser Ala Thr Ile Arg Glu
                565                 570                 575

Arg Gly Pro Val Trp Gln Lys Ser Phe Gly Ala Phe Ile Leu Thr Ala
                580                 585                 590

Ser His Asn Pro Gly Gly Pro Glu Glu Asp Phe Gly Ile Lys Tyr Asn
            595                 600                 605

Thr Gln Asn Gly Gly Pro Ala Pro Glu Tyr Leu Met Glu Ala Thr Tyr
            610                 615                 620

Ala Asn Thr Thr Cys Ile Lys Thr Tyr Lys Ile Cys Glu Asp Phe Pro
625                 630                 635                 640

Ser Ile Asp Ile Thr Gln Val Gly Ala Thr Thr Val Ala Ala Ala Asp
                645                 650                 655

Gly Ser Thr Ser Val Val Val Glu Val Ile Pro Ser Thr Gln Ser His
                660                 665                 670

Val Thr Leu Leu Lys Thr Ile Phe Asp Phe Pro Ala Ile Lys Ala Leu
            675                 680                 685

Leu Asp Arg Pro Asp Phe Ser Met Val Tyr Asp Ser Met His Gly Val
    690                 695                 700

Asn Gly Pro Phe Ser Lys Ala Val Phe Val Asp Glu Leu Gly Gln Pro
705                 710                 715                 720

Glu Ser Val Leu Arg Asn His Ile Pro Lys Asp Phe Ala Gly Gly
                725                 730                 735

His Ala Asp Pro Asn Leu Thr Tyr Ala Lys Glu Leu Val Lys Thr Met
```

|   |   |   | 740 |   |   |   | 745 |   |   |   | 750 |   |
|---|---|---|---|---|---|---|---|---|---|---|---|---|

Gly Leu Asp Arg Thr Gly Asn Lys Ile Asp Val Asp Gly Pro Ile Pro
         755                760                765

Ser Phe Gly Ala Ala Asp Gly Asp Arg Asn Met Ile Leu
  770               775                780

Gly Thr Gln Phe Phe Val Thr Pro Ser Asp Ser Leu Ala Val Ile Val
785                 790                795                800

Ala Asn Ala Asn Cys Ile Pro Phe Phe Ser Gln Gly Gly Leu Lys
                805                810              815

Ala Val Ala Arg Ser Met Pro Thr Ser Gly Ala Val Asp Arg Val Ala
        820                825              830

Lys Asp Leu Asn Leu Asp Phe Glu Thr Pro Thr Gly Trp Lys Phe
        835                840              845

Phe Gly Asn Leu Met Asp Ser Lys Ala Ile Phe Lys Gly Lys Asp Tyr
850                 855                860

Thr Pro Phe Ile Cys Gly Glu Glu Ser Phe Gly Thr Gly Ser Asp His
865                 870                875              880

Val Arg Glu Lys Asp Gly Ile Trp Ala Val Leu Ala Trp Leu Asn Ile
        885                890              895

Leu Ala Ala His Asn Pro Asp Ala Ser Lys Pro Leu Val Thr Val Glu
          900                905              910

Asp Ile Val Arg Lys His Trp Ser Lys Tyr Gly Arg Asn Tyr Tyr Cys
        915                920              925

Arg Trp Asp Phe Glu Gly Met Asp Ala Ala Gly Ala Asn Ala Met Met
        930                935              940

Glu Lys Met Arg Ala Asp Ala Ala Ser Asn Thr Gly Arg Thr Val Gly
945                 950                955              960

Ser Tyr Thr Ile Ala Thr Ala Asp Asp Phe Arg Tyr Val Asp Pro Val
                965                970              975

Asp Gly Ser Val Ala Ala Lys Gln Gly Ile Arg Phe Leu Met Ser Asp
        980                985              990

Gly Ser Arg Val Ile Phe Arg Leu Ser Gly Thr Ala Gly Ser Gly Ala
        995             1000            1005

Thr Val Arg Met Tyr Ile Glu Gln Tyr Glu Thr Glu Lys Leu Asp Leu
  1010               1015              1020            1

Pro Val Ala Ser Ala Leu Glu Glu Leu Thr Ser Ile Ala Leu Gln Leu
025                1030              1035              1040

Cys Asp Ile Lys Thr Phe Cys Gly Thr Glu Thr Pro Thr Val Ile Thr
        1045              1050              1055

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Phe Met Leu Met Asn Ser Phe Ser Thr
1                5

(2) INFORMATION FOR SEQ ID NO:9:

(i) SEQUENCE CHARACTERISTICS:
        (A) LENGTH: 19 amino acids

```
         (B) TYPE: amino acid
         (D) TOPOLOGY: linear (ii) MOLECULE TYPE: protein (xi) SEQUENCE DESCRIPTION: SEQ ID NO:9:

Ala Val Phe Val Asp Glu Leu Gly Gln Pro Glu Ser Val Leu Arg Asn
 1               5                  10                  15

His Ile Pro
```

ISOLATED GENE ENCODING AN ENZYME WITH UDP-GLUCOSE PYROPHOSPHORYLASE AND PHOSPHOGLUCOMUTASE ACTIVITIES FROM *CYCLOTELLA CRYPTICA*

The United States Government has rights in this invention under Contract No. DE-AC36-83CH10093 between the United States Department of Energy and the National Renewable Energy Laboratory, a Division of the Midwest Research Institute.

FIELD OF THE INVENTION

The invention relates to a cloned gene encoding an enzyme involved in the metabolism of carbohydrates in algae.

BACKGROUND OF THE INVENTION

The present invention relates to a cloned gene which encodes an enzyme, the purified enzyme, and the applications and products resulting from the use of the gene and enzyme.

Polysaccharides, sugars, and lipids are the primary constituents of many food and industrial products. These products are central to human and animal nutrition and therefore have significant commercial value. Crop plants are a primary source of these compounds. Numerous crop improvement efforts around the world are focused on altering the amounts and ratios of these compounds in various species.

Carbohydrates are a major form of energy storage in plants and animals. Long chain storage carbohydrates can take many forms, but most commonly are polymers of glucose molecules; these polymers are referred to as glucans. The glucose molecules in these polysaccharides can be joined together through a variety of different linkages. The storage polysaccharides starch and glycogen are α-1,4, linked glucans. Starch is the primary storage glucan in higher plants, and starch reserves in seeds comprise a major source of carbohydrate for human and animal nutrition and for the production of certain commodity chemicals such as ethanol. Glycogen is a common energy storage compound for animals and many microbes. β-1,3 linked glucans are present as storage carbohydrates in numerous algal taxa, including laminarin (Phaeophyceae), chrysolaminarin (Bacillariophyceae and Chrysophyceae), and paramylon (Euglenophyceae). The β-1,4 linked glucans include the structural polymer cellulose, which is one of the most abundant biological polymers on earth.

The biosynthetic pathways of all of these glucans share a common mechanistic theme: the basic building block (i.e, the substrate for chain elongation) is an activated glucose molecule. Activation is achieved by conjugation of glucose to a nucleoside diphosphate (NDP) such as uridine diphosphate (UDP) or adenosine diphosphate (ADP). Actual synthesis of the polymer is mediated by synthase enzymes (e.g., starch synthase), which utilize NDP-glucose molecules as substrates. The general reaction catalyzed by glucan synthases is shown below:

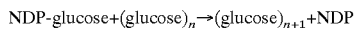

NDP-glucose+(glucose)$_n$→(glucose)$_{n+1}$+NDP

Sucrose is the principal carbon transport molecule in higher plants and is an important food ingredient. The biosynthesis of sucrose also utilizes a nucleoside diphosphate-activated glucose molecule, generally UDP-glucose. The biosynthesis of many other disaccharides and complex sugars also uses NDP-glucose as a substrate.

Specific enzymes are responsible for formation of the NDP-glucose molecules that are used for glucan and complex sugar biosynthesis. UDP-glucose is formed through the action of the enzyme UDP-glucose pyrophosphorylase (E.C. 2.7.7.9; also known as glucose-1-phosphate uridylyltransferase, and hereinafter referred to as UGPase). The reaction catalyzed by UGPase is as follows:

glucose-1-phosphate+UTP→UDP-glucose+PP$_i$ where UTP is uridine triphosphate and PP$_i$ is pyrophosphate. The subsequent hydrolysis of pyrophosphate to orthophosphate is responsible for driving the reaction toward the formation of UDP-glucose. UGPase genes have been cloned from disparate sources, including potato (Katsube et al., J. Biochem. 108: 321–326 (1990)), human (Peng and Chang, FEBS Lett. 329:153–158 (1993)), and yeast (Purnelle et al., Yeast 8:977–986 (1992)). The UGPase enzyme has also been purified from various sources, including barley (Elling and Kula, J. Biotechnol. 34:157–163 (1994)), rice (Kimura et al., Plant Physiol. Biochem. 30:683–693 (1992)), and potato (Nakano et al., J. Biochem. 106:528–532 (1989)).

The substrate for UGPase, glucose-1-phosphate, is synthesized from glucose-6-phosphate through the action of the enzyme phosphoglucomutase (E.C. 5.4.2.2; hereinafter referred to as PGMase), as shown below:

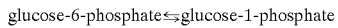

glucose-6-phosphate⇌glucose-1-phosphate

The PGMase enzyme has been purified from many sources, including pea (Galloway and Dugger, Physiol. Plant. 92:479–486 (1994)), human (Fazi et al., Prep. Biochem. 20:219–240 (1990)), and Lactobacillus (Marechal et al., Arch. Biochem. Biophys. 228:592–599 (1984)). The PGMase gene has also been cloned from a number of sources, including human (Putt et al., Biochem. J. 296:417–422 (1993)), yeast (GenBank accession no. X72016), and *E. coli* (GenBank accession no. U08369).

The present invention concerns a novel carbohydrate biosynthesis gene isolated from a microalga. Microalgae are defined as unicellular, eukaryotic algae. Although their current biotechnological utilization is primarily for the production of high value specialty products, microalgae have very high productivity rates that could support the large-scale, commercial production of lower value carbohydrates and lipids. One of the species under consideration for such uses is the centric diatom *Cyclotella cryptica*. This organism grows naturally in salt water and has been shown to be highly productive in outdoor culture (Weissman and Tillett, NREL/TP-232-4147:32–56, (1989)). *C. cryptica* is under consideration for the production of alternative fuels because lipids can comprise up to 40–60% of the cellular dry weight when cells are grown under nutrient-limiting conditions. These lipids are similar in composition to the triacylglycerols produced by oilseed crops and can be readily converted, via transesterification with a simple alcohol, into a diesel fuel replacement.

In addition to its ability to accumulate lipids, *C. cryptica* produces a substantial amount of carbohydrate. Approximately 20–30% of the dry weight of *C. cryptica* cells consists of a β-1,3 linked glucan referred to as chrysolaminarin (Roessler, J. Phycol. 23:494–498 (1987)). This glucan accumulates in all growth phases and decreases only slightly upon the induction of lipid accumulation in nutrient-deficient cells. Thus, this carbohydrate constitutes a significant sink for fixed carbon, and therefore competes for carbon substrates with the lipid biosynthetic pathway. Roessler (Roessler, J. Phycol. 23:494–498 (1987)) demonstrated previously that the precursor for chrysolaminarin biosynthesis in C. cryptica is UDP-glucose, and that UGPase enzyme activity was present in extracts of C. cryptica cells. The UDP-glucose produced by UGPase is a substrate for the enzyme chrysolaminarin synthase, which adds glucose units successively onto the growing carbohydrate polymer. In contrast, PGMase in C. cryptica has not been characterized.

The instant invention is directed to the isolation of a gene from C. cryptica that encodes a multifunctional enzyme that has both UGPase and PGMase activities. This is the first report of the isolation of a gene encoding either of these enzymes from an alga. The fact that UGPase and PGMase domains are both present on a single polypeptide chain could not have been anticipated; these activities have never before been reported to exist together on a single protein. Uttaro and Ugalde (Uttaro and Ugalde, Gene 150:117–122 (1994)) reported a chromosomal cluster in the bacterium *Agrobacterium tumefaciens* that encodes ADP-glucose pyrophosphorylase, glycogen synthase, and PGMase; however, the three activities are encoded by three separate open reading frames, and are consequently found on three separate proteins. The presence of UGPase and PGMase on a single polypeptide chain could have significant advantages both in terms of more favorable reaction kinetics and because a single gene can be inserted into an organism via genetic engineering to affect two enzymatic functions simultaneously. Artificial polypeptide fusions have been shown to have kinetic advantages in other systems (for example, Tamada et al., Bioconjugate Chem. 5:660–665 (1994)). A naturally-occurring fusion may exhibit even greater kinetic advantages than man-made fusions, in that evolutionary selective pressure can result in functionally superior enzymes.

SUMMARY OF THE INVENTION

An object of this invention is to affect the production of storage compounds in biological organisms.

Another object of this invention is to develop plant, algal, or microbial species that produce more or less carbohydrate, sugar (including sucrose), or lipid.

Another object of this invention is to provide a protein having two enzymatic activities.

Another object of this invention is to provide a protein having two enzymatic activities wherein the activities are UGPase and PGMase.

Another object of this invention is to provide a single gene encoding a protein having two enzymatic activities.

Another object of this invention is to provide a single gene encoding a protein having two enzymatic activities wherein the activities are UGPase and PGMase.

Another object of this invention is to develop strains of *C. cryptica* and related microalgae that produce more lipid through the inactivation or inhibition of competing carbohydrate biosynthetic pathways.

To accomplish these goals, a gene encoding UGPase and PGMase has been isolated and cloned from *C. cryptica*. In this organism, the two enzymes are present as separate domains on a single polypeptide chain, which is encoded by a single gene. The protein encoded by this gene has been purified to near homogeneity and has been shown to carry out both enzymatic activities in vitro. The gene could be overexpressed in plants, algae, or other microorganisms in order to increase PGMase and UGPase activities in vivo, thus potentially altering the amounts or ratios of carbohydrate, sugar (including sucrose), or lipid produced. The expression of the gene could be inhibited in *C. cryptica* or a related species by introduction of antisense, ribozyme, co-suppression, or other constructs that are based on the DNA sequence of this gene.

BRIEF DESCRIPTION OF THE DRAWINGS

FIG. 4A illustrates overexpression of the UGPase/PGMase (upp1) gene in recombinant *C. cryptica* cells, as determined via the measurement of UGPase activity. The white and gray bars represent the results from two independent experiments. Error bars for the control data indicate ± one standard deviation around the mean for six independent strains transformed with a control plasmid. One Unit (U) of activity is defined as one nmol of product formed per minute.

FIG. 4B illustrates overexpression of the upp1 gene in recombinant *C. cryptica* cells, as determined via the measurement of PGMase activity. The white and gray bars represent the results from two independent experiments. Error bars for the control data indicate ± one standard deviation around the mean for six independent strains transformed with a control plasmid. One Unit (U) of activity is defined as one nmol of product formed per minute.

DESCRIPTION OF THE PREFERRED EMBODIMENTS

Figure 1:
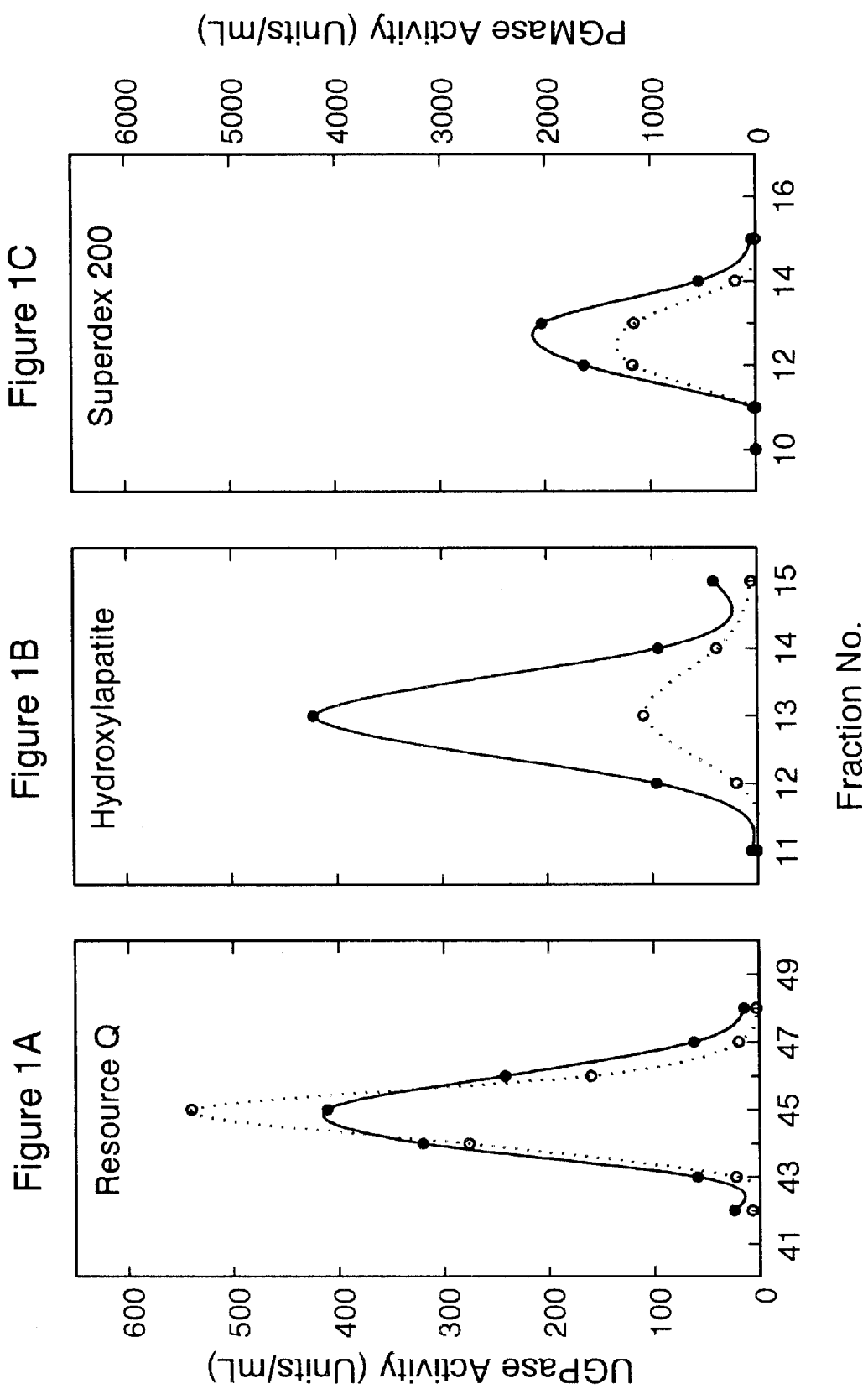
FIG. 1A illustrates UGPase and PGMase activity in 1.5 mL fractions eluting from a 6 mL Resource Q ion exchange chromatography column (Pharmacia Biotech, Inc.; Piscataway, N.J.). UGPase activity is represented by a solid line, and PGMase activity is represented by a dotted line. One Unit of activity is defined as one nmol of product formed per minute. Note that the activities of UGPase and PGMase co-elute.
FIG. 1B illustrates UGPase and PGMase activity in one mL fractions eluting from a 7×52 mm Bio-Scale CHT2-1 hydroxylapatite chromatography column (BioRad Laboratories; Hercules, Calif.). UGPase activity is represented by a solid line, and PGMase activity is represented by a dotted line. One Unit of activity is defined as one nmol of product formed per minute. Note that the activities of UGPase and PGMase co-elute.
FIG. 1C illustrates UGPase and PGMase activity in one mL fractions eluting from a 1×30 cm Superdex 200 gel filtration chromatography column (Pharmacia Biotech, Inc.; Piscataway, N.J.). UGPase activity is represented by a solid line, and PGMase activity is represented by a dotted line. One Unit of activity is defined as one nmol of product formed per minute. Note that the activities of UGPase and PGMase co-elute.

The gene for UGPase and PGMase (hereinafter referred to as the upp1 gene) from *C. cryptica* encodes a polypeptide that is 1056 amino acids in length and that has a predicted molecular weight of 114.4 kilodaltons. UGPase and PGMase enzyme functions are both present on this single polypeptide. The genomic sequence contains three introns, which are 290, 103, and 76 base pairs (bp) in length.

Standard cloning techniques were performed as described in Sambrook et al. (*Molecular Cloning: A Laboratory Manual*, Cold Spring Harbor Laboratory Press (1989)), and the terminology herein is used as defined in that reference. Unless specifically defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

EXAMPLE

For the experiments below, the strain *Cyclotella cryptica* T13L was used. This strain was obtained from the Bigelow Laboratory Culture Collection of Marine Phytoplankton, West Boothbay Harbor, Me. *C. cryptica* was cultured as described in Roessler (Roessler, J. Phycol. 24: 394–400 (1988)).

Cloning of the upp1 Gene

The *C. cryptica* upp1 gene was isolated as follows. A fragment of the gene was first produced by the polymerase chain reaction (PCR) using degenerate oligonucleotide primers that were based on conserved sequences from other known UGPase genes, specifically potato (Katsube et al., J. Biochem. 108:321–326 (1990)), human (Peng and Chang, FEBS Lett. 329:153–158 (1993)), yeast (Purnelle et al., Yeast 8: 977 986 (1992)), and Dictyostelium (Ragheb and Dottin, Nucleic Acids Res. 15:3891–3906 (1987)). Three primers were designed that are referred to as UP2, UP3, and UP4. UP3 is an upstream primer; UP2 and UP4 are downstream primers, with UP4 being further downstream than UP2. The DNA sequences for the primers are given as follows (using IUPAC codes):

UP2: 5'-ARRTTRTTNGTRTTRAA (17-mer, 128-fold degenerate) also identified herein as SEQ ID NO:1.

UP3: 5'-TGGTAYCCNCCNGGWCA (17-mer, 64-fold degenerate) also identified herein as SEQ ID NO:2.

UP4: 5'-GCNGTYTCNARYTG (14-mer, 128-fold degenerate) also identified herein as SEQ ID NO:3.

A nested PCR strategy was used to isolate a portion of the upp1 gene. First, primers UP3 and UP4 were used in a PCR amplification with the following conditions; a 20 µl PCR reaction contained 36 ng of total DNA from *C. cryptica*, 2.5 µM of each primer, 10 mM Tris-Cl (pH 8.3), 50 KCl, 1.5 mM MgCl$_2$, 0.2 mM dNTPs, and 0.75 units of Taq DNA polymerase (Perkin Elmer-Cetus; Norwalk, Conn.). Total DNA was isolated from *C. cryptica* by the method of Jarvis et al. (Jarvis et al., J. Phycol. 28:356–362 (1992)). The following thermal cycle was used; Step 1, 94° C. for 2 min; Step 2, 45° C. for 30 sec; Step 3, 72° C. for 1 min; Step 4, 94° C. for 30 sec; Step 5, 45° C. for 30 sec; Step 6, repeat steps 3 to 5 for 30 times total; and Step 7, 72° C. for 10 min. The products of this reaction were analyzed on a 2.8% agarose gel, which indicated a large number of non-specific DNA products.

The products of this first amplification were subjected to a secondary, nested amplification using primers UP3 and UP2. The conditions for this amplification were identical to the first except that 0.1 µl of the first reaction was used as the template, and only 20 cycles were run instead of 30. The products of this reaction were also analyzed by gel electrophoresis and exhibited 10 to 15 distinct DNA products. One of the DNA products was 338 bp in length, which was the expected size based on the sequences of the other known UGPase genes. This fragment was cut from the gel, purified by use of a "Gene Clean" kit (BIO 101; La Jolla, Calif.), and reamplified with primers UP2 and UP3 using the previous reamplification conditions.

The product of this third reaction was subcloned into the plasmid pCRII (Invitrogen; San Diego, Calif.) according to the manufacturer's instructions, and the resulting product was used to transform *E. coli* INVαF'. The cloned fragment was sequenced by the double-stranded sequencing protocol of Kraft et al. (Kraft et al., Biotechniques 6:544–546 (1988)). The 338-bp DNA fragment contained 304 bp of amplified *C. cryptica*-derived sequence; 34 bp were derived from the amplification primers. This *C. cryptica* DNA sequence is identified herein as SEQ ID NO:4. The deduced amino acid sequence of this fragment (identified herein as SEQ ID NO:5) exhibited 37% identity with the corresponding sequence of potato UGPase, thereby confirming that a *C. cryptica* UGPase gene fragment had been purified.

The cloned PCR product was subsequently used as a probe to isolate a lambda clone containing the entire *C. cryptica* UGPase gene. The lambda library used was constructed as described in Roessler and Ohlrogge (Roessler and Ohlrogge, J. Biol. Chem. 268:19254–19259 (1993)). Filter lifts of the library were screened with the cloned 338-bp UGPase gene fragment that was labeled via PCR with digoxygenin using the "Genius" non-radioactive labeling and detection system (Boehringer Mannheim Corporation; Indianapolis, Ind.) according to the manufacturer's instructions. Several positive clones were isolated in this manner. Restriction mapping and subcloning were used to identify a DNA segment shared by all of the positive clones. Sequencing of this DNA segment revealed that it contained a single long open reading frame, the 5' end of which showed homology to known UGPase genes and the 3' end of which showed homology to known PGMase genes. PGMase and UGPase are thought to catalyze successive steps in the chrysolaminarin biosynthesis pathway. The isolation of a naturally occurring fusion of these two genes is, to our knowledge, unprecedented, and this result could not have been anticipated.

Three introns were identified within the upp1 coding region. Exact splice junctions were determined by sequencing the PCR products made from *C. cryptica* cDNA. RNA was isolated as described in Roessler and Ohlrogge (Roessler and ohlrogge, J. Biol. Chem. 268:19254–19259 (1993)), and subjected to reverse transcription and PCR using a kit (GeneAmp RNA PCR Kit; Perkin-Elmer Cetus; Norwalk, Conn.). Gene-specific primers based on the *C. cryptica* upp1 gene sequence were used. The DNA products of these amplifications were subcloned into pCRII and sequenced as described above. The three introns identified by this method are 290, 103, and 76 bp in length.

The DNA sequence of the upp1 gene, from the start codon through the stop codon, is identified herein as SEQ ID NO:6. The positions of the three introns are noted. The genomic sequence including the start and stop codons is 3640 bp in length; removal of the introns yields a 3171-bp coding sequence. The deduced amino acid sequence of the UGPase/PGMase protein is identified herein as SEQ ID NO:7. The predicted polypeptide is 1056 amino acids in length with a molecular weight of 114.4 kilodaltons. Based on similarities to known sequences, the boundary between the UGPase and PGMase domains is located approximately at position 480 in the amino acid sequence.

Purification of the UGPase/PGMase protein

To further characterize the protein encoded by the cloned upp1 gene, several sequential column chromatographic procedures were carried out to purify the native UGPase/PGMase protein. The cells in one liter of an exponential phase culture were harvested by centrifugation at 15,000×g for 10 minutes, followed by washing with 8 mL of Buffer A (50 mM HEPES buffer, pH 7.5, containing 2 mM dithiothreitol) and repelleting by another centrifugation step. The cells were resuspended in 8 mL of Buffer A, frozen in liquid $N_2$, and then stored at −80° C. Cell-free extracts were prepared by subjecting the cells to three rounds of freezing in liquid $N_2$ and thawing at 30° C., followed by centrifugation at 37,000×g for 20 minutes. The extract was then filtered through a 0.2 µm filter.

Ion exchange chromatography was carried out by loading 4 mL of the filtered extract onto a 6 mL Resource Q anion exchange column (Pharmacia Biotech, Inc.; Piscataway, N.J.), followed by elution with a 120 mL linear gradient from 0 to 0.5M NaCl in Buffer A. Fractions (1.5 mL) were collected and independently assayed for the presence of UGPase and PGMase activities as described below. As shown in FIG. 1A, UGPase and PGMase activities were found in the same fractions; the peak activities eluted at a NaCl concentration of approximately 270 to 300 mM.

The active fractions from the ion exchange chromatography step were combined and desalted by passage through a 20 mL Hi-Trap desalting column (Pharmacia Biotech, Inc; Piscataway, N.J.) that had been equilibrated with Buffer A. The desalted solution was loaded onto a 7×52 mm Bio-Scale CHT2-1 hydroxylapatite column (BioRad Laboratories; Hercules, Calif.), and eluted with a 24 mL linear gradient from 0 to 0.5M sodium phosphate in Buffer A. One mL fractions were collected and independently assayed for the presence of UGPase and PGMase activities as described in the "Enzyme Assays" section below. As shown in FIG. 1B, UGPase and PGMase activities were found in the same fractions, which eluted at a sodium phosphate concentration of approximately 270 to 290 mM.

The active fractions from the hydroxylapatite chromatography step were combined and concentrated to 0.2 mL by the use of a Centricon-30 ultrafiltration device (Amicon, Inc.; Beverly, Mass.). This solution was loaded onto a 1×30 cm Superdex 200 gel filtration column (Pharmacia Biotech, Inc.; Piscataway, N.J.) that had been equilibrated with Buffer A. One mL fractions were collected and independently assayed for the presence of UGPase and PGMase activities. As shown in FIG. 1C, UGPase and PGMase activities were once again found in the same fractions.

Figure 2:
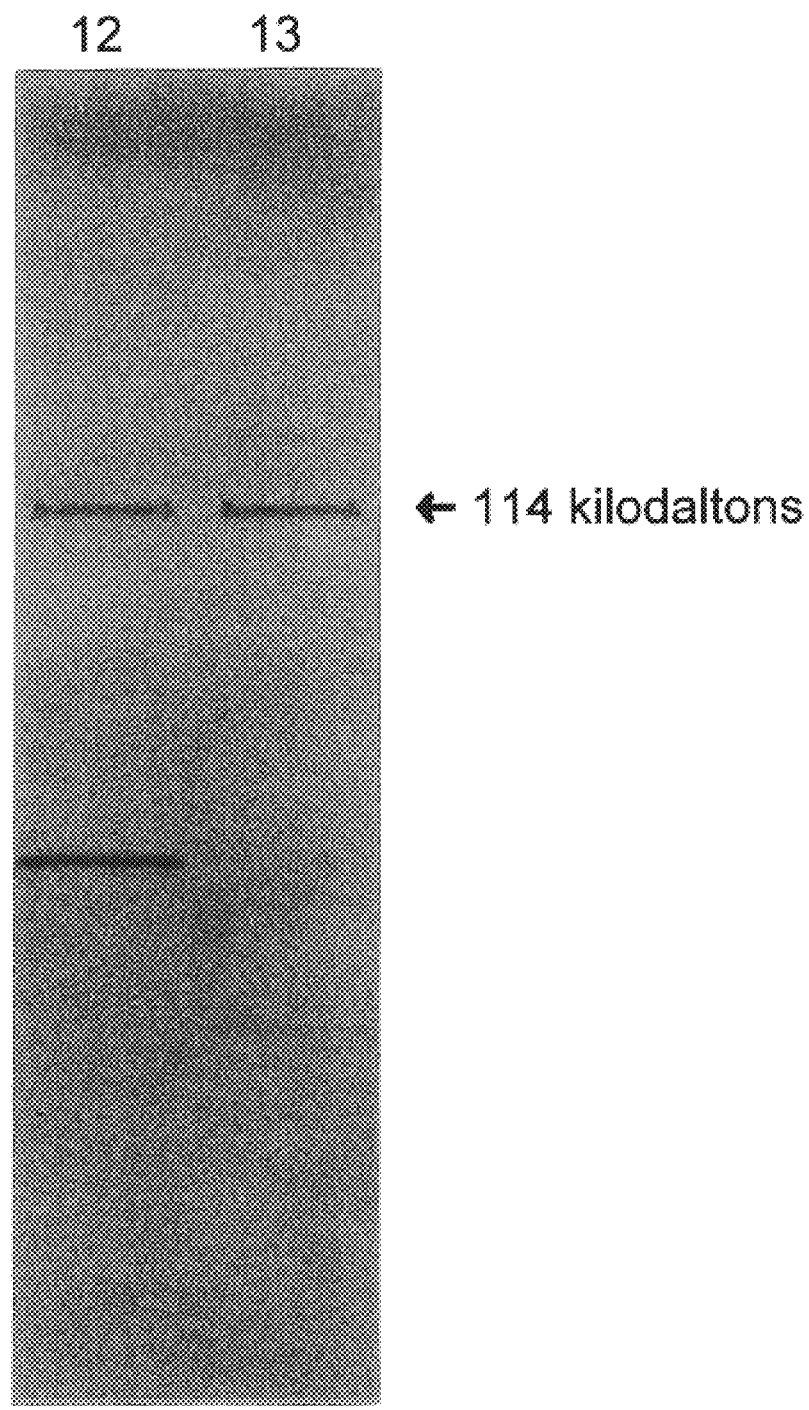
FIG. 2 is a photograph of a sodium dodecyl sulfate-polyacrylamide gel (10% polyacrylamide, w/w) that has been stained with Coomassie Blue R-250, showing a substantially purified preparation of the UGPase/PGMase protein. The molecular weight of the purified protein was estimated to be 114 kilodaltons based on the migration distances of protein standards. The number above each lane represents the fraction number from the gel filtration chromatography step illustrated in FIG. 1C above.

The size exclusion chromatography fractions containing UGPase and PGMase activities were subjected to electrophoresis through an sodium dodecyl sulfate polyacrylamide gel (10% polyacrylamide, w/w) to determine the degree of purification. Thirty µL from each fraction were loaded per lane, and after electrophoresis the proteins in the gel were visualized by staining with Coomassie Blue R250. These results are shown in FIG. 2. Fractions number 12 and 13 had approximately equal activities; both of these fractions contained a 114 kilodalton protein that stained with equal intensity in both fractions. In fraction 13, this protein was purified to near homogeneity, providing strong evidence that this was the UGPase/PGMase protein encoded by the cloned upp1 gene.

Enzyme Assays

UGPase activity was assayed by measuring the conversion of [$^{14}$C]glucose-1-phosphate to [$^{14}$C]UDP-glucose. The assay was carried out essentially as described by Roessler (Roessler, J. Phycol. 24:394–400 (1988)), in which [$^{14}$C]glucose-1-phosphate is incubated with UTP in the presence of UGPase for a specified period of time, after which the remaining substrate is dephosphorylated and the radioactively-labeled product ([$^{14}$C]UDP-glucose) is bound onto DEAE-filter paper for liquid scintillation counting. The reaction mixture contained 50 mM Hepes buffer (pH 7.8), 5 mM $MgCl_2$, 1 mM UTP, and 0.5 mM [$^{14}$C]glucose-1-phosphate (American Radiolabeled Chemicals, Inc.; St. Louis, Mo. at a specific activity of 1 mCi/mmol. Enzyme extract was added to tubes containing prewarmed reaction mixtures to begin the reaction, which was then allowed to proceed for 15 minutes at 30° C. The reaction was terminated by placing the tubes into boiling water for 3 minutes, followed by cooling on ice. For the dephosphorylation reaction, 0.5 units of bacterial alkaline phosphatase (Sigma Chemical Co.; St. Louis, Mo.; catalog no. P-4252) were added to each reaction and incubated for one hour at 30° C. The reaction mixtures were spotted onto separate 2.5 cm DE81 filter disks (Whatman Inc.; Fairfield, N.J.), which were then washed in five consecutive batches of water (200 mL each). The radioactivity of each filter was determined by liquid scintillation counting. Experiments utilizing glucose-6-phosphate for $K_m$ determinations were performed in the same fashion except that [$^{14}$C]glucose-6-phosphate (American Radiolabeled Chemicals, Inc.; St. Louis, Mo.) was used as the substrate and 10 µM glucose-1,6-diphosphate was included in the reactions.

PGMase activity was measured in a coupled assay in which glucose-6-phosphate is produced from glucose-1-phosphate via the action of PGMase, and then converted to 6-phosphogluconate through the action of exogenously added glucose-6-phosphate dehydrogenase with the subsequent reduction of $NADP^{30}$ to NADPH, which is measured spectrophotometrically by recording the change in absorbance at 340 nm. The reaction mixture contained 50 mM HEPES (pH 7.8), 5 mM $MgCl_2$, 1 mM $NADP^+$, 0.5 mM glucose-1-phosphate, 10 µM glucose-1,6-diphosphate, one unit of glucose-6-phosphate dehydrogenase (Boehringer Mannheim Corporation; Indianapolis, Ind.; catalog no. 165875), and enzyme extract. The reaction was carried out at 25° C. for 2.5 minutes.

Amino Acid Sequencing of the Purified UGPase/PGMase Protein

The co-elution of UGPase and PGMase activities throughout the course of the protein purification procedure, along with the presence of a nearly pure 114 kilodalton polypeptide after the final size exclusion chromatography step, provided strong evidence that the protein product of the upp1 gene had been purified. In order to provide absolute confirmation that the purified protein was the product of the cloned upp1 gene, partial amino acid sequences were determined for peptides produced from the purified protein via proteolytic digestion. These sequences were then compared to the amino acid sequence deduced from the DNA sequence of the upp1 gene.

The purified polypeptide that migrated at 114 kilodaltons during polyacrylamide gel electrophoresis was excised from the gel, and the gel slice was incubated in 0.1M ammonium bicarbonate containing 0.1% Tween 20 and lysyl peptidase. The resulting peptides were extracted twice with 200 µL of 50% acetonitrile containing 0.1% trifluoroacetic acid (TFA). The combined extracts were concentrated to 200 µL via vacuum centrifugation and diluted to 600 µL with 0.1% TFA. This sample was loaded onto a reverse phase high performance liquid chromatography column (2.1×30 mm Brownlee C18 Aquapore ODS column; Applied Biosystems, Inc.; Foster City, Calif.) and separated with the following gradient: 5% B for 5 min, 5% B to 40% B over the next 45 min, and then 40% B to 70% B over the final 5 min; where A=0.1% TFA in water and B=0.09% TFA in acetonitrile. Two individual peptides resolved in this manner were sequenced via automated Edman degradation. The amino acid sequences determined for these two peptides are identified herein as SEQ ID NO:8 and SEQ ID NO:9. These sequences were identical to amino acid sequences predicted by the DNA sequence of the upp1 gene, confirming that the substantially purified protein was the product of the upp1 gene. SEQ ID NO:8 corresponds to positions 119 through 127 of the deduced amino acid sequence of the UGPase/PGMase protein (i.e., SEQ ID NO:7), whereas SEQ ID NO:9 corresponds to positions 711 through 729 of the deduced amino acid sequence of the UGPase/PGMase protein.

K Determinations

Figure 3A:
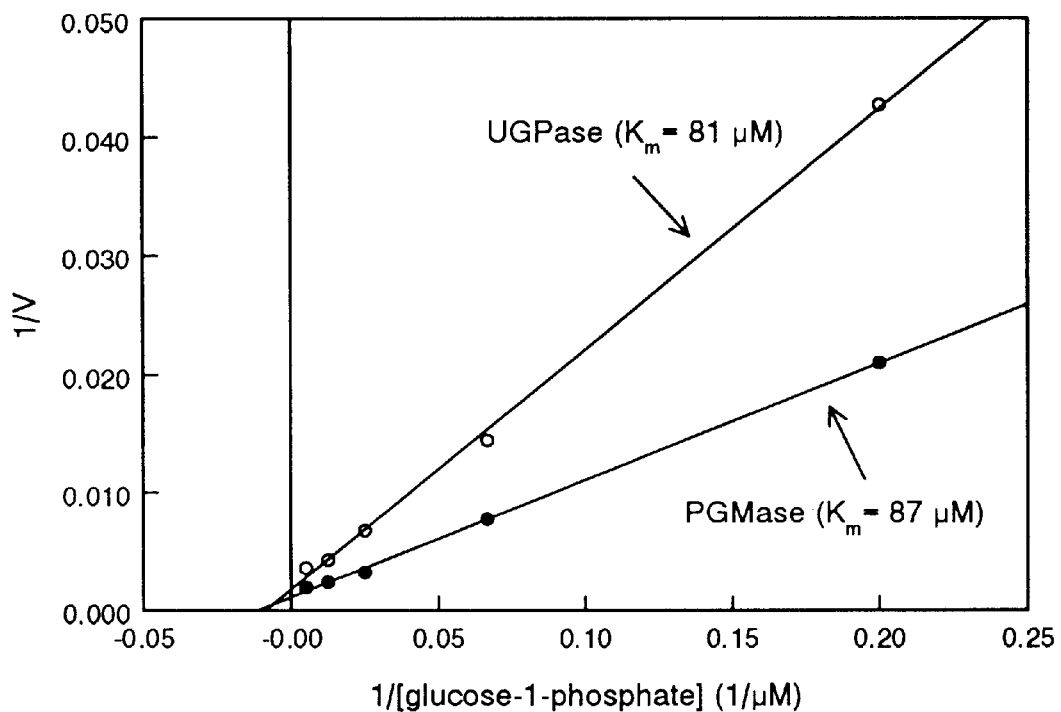
FIG. 3A illustrates double reciprocal plots of UGPase and PGMase activity versus glucose-1-phosphate concentration. Velocity (V) is expressed in Units/mL. UGPase activity is represented by open circles, and PGMase activity is represented by filled circles.

The $K_m$ for glucose-1-phosphate was determined for both the UGPase and PGMase portions of the UGPase/PGMase enzyme via standard procedures (i.e., double reciprocal plots of enzyme activity versus glucose-1-phosphate concentration), using a highly purified preparation of the enzyme. The results of these experiments are shown in FIG. 3A. The $K_m$ for glucose-1-phosphate was determined to be 81 μM for the UGPase portion and 87 μM for the PGMase portion of the enzyme.

Figure 3B:
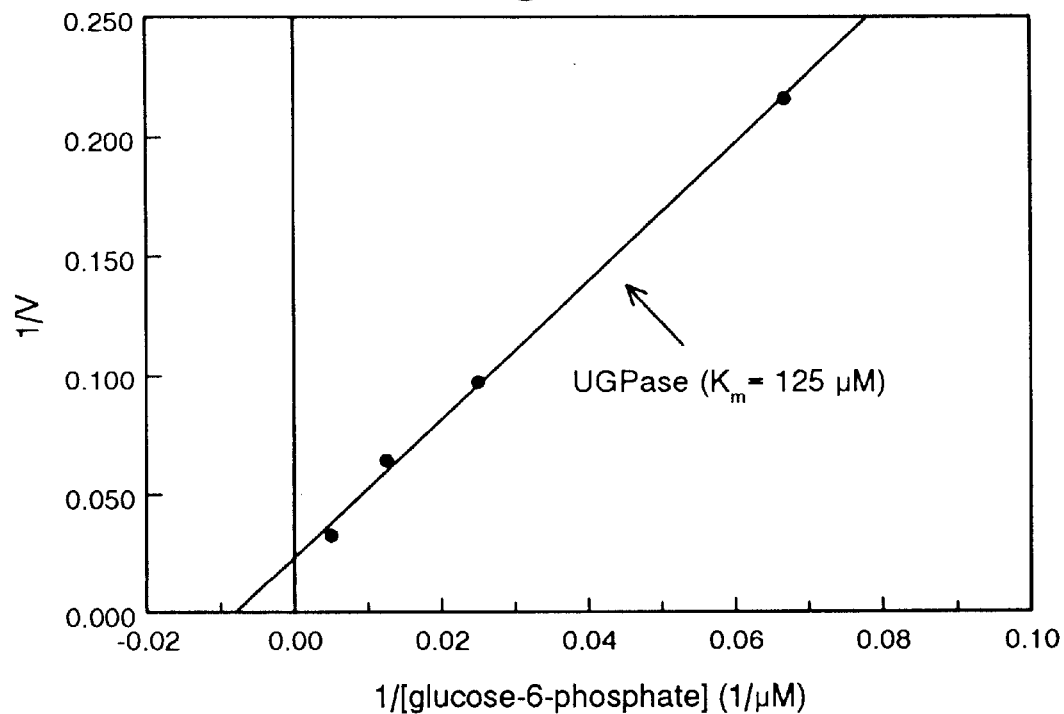
FIG. 3B illustrates a double reciprocal plot of UGPase activity versus glucose-6-phosphate concentration. Velocity (V) is expressed in Units/mL.

The conversion of glucose-6-phosphate to UDP-glucose was also measured for the purified enzyme (FIG. 3B). The maximum velocity of UDP-glucose formation (as determined via double reciprocal plots) was 13-fold less for glucose-6-phosphate than for glucose-1-phosphate. The $K_m$ for glucose-6-phosphate in this reaction was 125 μM. These results confirm that the purified UGPase/PGMase protein, which is encoded by the upp1 gene, is able to catalyze the formation of UDP-glucose from glucose-6-phosphate. A single enzyme has never previously been discovered or purified that is able to catalyze this reaction.

Overexpression Studies

Additional copies of the upp1 gene were introduced back into C. cryptica to demonstrate that the gene confers the predicted activities in vivo. Plasmid pANUP contains a ~6-kilobase C. cryptica genomic DNA fragment inserted into the KpnI/EcoRI sites upstream of the nptII gene of plasmid pANRz. pANRz is identical to pACCNPT10 (Dunahay, et al., J. Phycol. 31:1004–1012 (1995)) except that the downstream Bpu1102/PstI fragment is replaced by a BglII/MluI adaptor sequence. The inserted C. cryptica fragment contains the entire coding sequence of the upp1 gene (including introns), as well as 763 bp of noncoding sequence 5' to the coding sequence and approximately 1600 bp of noncoding sequence 3' to the coding sequence. This plasmid was used to transform wild-type C. cryptica cells according to the particle bombardment transformation protocol of Dunahay et al. (Dunahay et al., J. Phycol. 31:1004–1012 (1995)). Approximately 5 μg of plasmid was precipitated onto tungsten microcarriers, and 10 μL of the coated particles were used for each bombardment. Plasmid pANRz, which does not contain the upp1 gene, was used as a control. Bombarded cells were given 2 days to recover before being transferred to selection plates. The transformants were selected based on their resistance to the antibiotic G418 and appeared after about one week. Individual transformants were trasnferred to liquid 50% ASW medium (Brown, Phycologia 21:408–410 (1982)) and cultured at 26° C. without agitation, under a light intensity of 50 $\mu E.m^{-2}.sec^{-1}$. Cells were harvested for enzyme assays at early stationary phase; 15 mL of each culture were centrifuged at 2000×g for 5 minutes. The cell pellet was resuspended in 5 mL of Hepes buffer, pH 7.8, containing 2 mM dithiothreitol, and recentrifuged. The final cell pellet was resuspended in 0.3 mL of the same buffer. The cell suspension was frozen on dry ice and stored at −80° C. Cell-free extracts were prepared by thawing the frozen cells on ice and centrifuging at 16,000×g for 15 min at 4° C. The protein concentrations of the supernatants were measured, and each extract was diluted with the same buffer to protein concentrations of 0.4 and 0.1 mg/mL. UGPase assays were carried out as described in the "Enzyme Assays" section above, using 2 μL of the 0.1 mg protein/mL enzyme extracts. PGMase assays were conducted as described in the "Enzyme Assays" section above, using 50 μL of the 0.4 mg protein/mL enzyme extracts.

The results of assays on 8 transformants are shown in FIG. 4A and FIG. 4B. The activities of both UGPase and PGMase were higher in transformants containing plasmid PANUP than in transformants containing the control plasmid pANRz, indicating that overexpression of the upp1 gene was achieved. Furthermore, these results suggest that the inserted recombinant upp1 gene is expressed to produce an enzyme with both UGPase and PGMase activities in vivo.

While various embodiments of the present invention have been described in detail, modifications and adaptations of those embodiments will be apparent to those skilled in the art. It is to be expressly understood, however, that such modifications and adaptations are within the scope of the present invention, as set forth in the following claims.

What is claimed is:

1. An isolated and purified DNA encoding a protein from *Cyclotella cryptica* comprising an enzyme selected from the group consisting of:
    (a) UDP-glucose pyrophosphorylase;
    (b) phosphoglucomutase; and
    (c) UDP-glucose pyrophosphorylase and phosphoglucomutase.

2. The DNA of claim 1 wherein the selected enzyme are UDP-glucose pyrophosphorylase and phosphoglucomutase.

3. The DNA according to claim 1 wherein the amino acid sequence of the encoded protein is the sequence identified as SEQ ID NO:7.

4. A vector comprising the DNA of claim 1.

5. A vector comprising the DNA of claim 3.

6. A host containing the vector of claim 4.

7. A host containing the vector of claim 5.

8. A host containing the vector of claim 5, wherein said host is *Cyclotella cryptica*.

9. An isolated and purified DNA having the sequence identified as SEQ ID NO:6.

10. The DNA of claim 9 wherein the DNA encodes UDP-glucose pyrophosphorylase and phosphoglucomutase.

11. An isolated and purified DNA from *Cyclotella cryptica* encoding UDP-glucose pyrophosphorylase and phosphoglucomutase.

* * * * *